United States Patent [19]
Shibata et al.

[11] Patent Number: 4,914,106
[45] Date of Patent: Apr. 3, 1990

[54] COMPOSITIONS AND METHODS EMPLOYING 2-OXA- OR -AZA-PREGNAN COMPOUNDS FOR INHIBITING ANDROGEN OR SUPPLYING PROGESTIN IN MAMMALS

[75] Inventors: Kenyu Shibata, Inagi; Nobuaki Yamakoshi, Kawasaki; Naoyuki Koizumi, Kawasaki; Shigehiro Takegawa, Kawasaki; Eiichiro Shimazawa, Sagamihara; Mamoru Mieda, Ebina, all of Japan

[73] Assignee: Teikoku Hormone Mfg. Co., Ltd., Tokyo, Japan

[21] Appl. No.: 228,316

[22] Filed: Aug. 4, 1988

Related U.S. Application Data

[62] Division of Ser. No. 833,715, Feb. 27, 1986, Pat. No. 4,785,103.

[30] Foreign Application Priority Data

Mar. 7, 1985 [JP] Japan .................................. 60-43731
Mar. 7, 1985 [JP] Japan .................................. 60-43732

[51] Int. Cl.$^4$ ..................... A61K 31/585; A61K 31/57
[52] U.S. Cl. ..................................... 514/284; 514/453; 546/78; 549/276
[58] Field of Search ..................... 546/78; 549/276; 514/284, 453

[56] References Cited

U.S. PATENT DOCUMENTS

| | | | |
|---|---|---|---|
| 3,080,381 | 3/1963 | Pappo | 549/276 X |
| 3,179,658 | 4/1965 | Hirschmann et al. | 549/276 X |
| 3,280,133 | 10/1966 | Pappo et al. | 546/77 |
| 3,290,287 | 12/1966 | Mazur et al. | 546/77 X |
| 4,732,897 | 3/1988 | Cainelli et al. | 514/284 X |

FOREIGN PATENT DOCUMENTS

| | | | |
|---|---|---|---|
| 0193871 | 9/1986 | European Pat. Off. | 546/78 |
| 1277754 | 6/1982 | United Kingdom . | |

OTHER PUBLICATIONS

Applezweig, "Steroid Drugs", McGraw-Hill Book Co., New York (1962), pp. 340–341, 344, 614–615.
Djerassi, "Steroid Reactions, An Outline for Organic Chemists", Holden–Day, Inc., San Francisco (1963), p. 242.
Nace et al., J. Organic Chem., vol. 31, pp. 2109–2115 (1966).

*Primary Examiner*—Diana G. Rivers
*Attorney, Agent, or Firm*—Wenderoth, Lind & Ponack

[57] ABSTRACT

A compound represented by the following formula

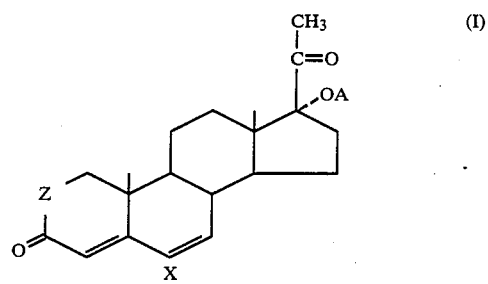

wherein A represents a hydrogen atom or a lower alkanoyl group, Z represents an oxygen atom or the group

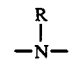

in which R represents a hydrogen atom or a lower alkyl group, and X represents a halogen atom, the compound being useful for controlling androgen-dependent diseases, particularly for preventing abortion or for contraception.

8 Claims, No Drawings

COMPOSITIONS AND METHODS EMPLOYING 2-OXA- OR -AZA-PREGNAN COMPOUNDS FOR INHIBITING ANDROGEN OR SUPPLYING PROGESTIN IN MAMMALS

This is a Rule 60 Divisional of Ser. No. 833,715 filed Feb. 27, 1986 now U.S. Pat. No. 4,785,103.

This invention relates to novel 2-oxa- or -aza-pregnane compounds. More specifically, it relates to compounds represented by the following formula

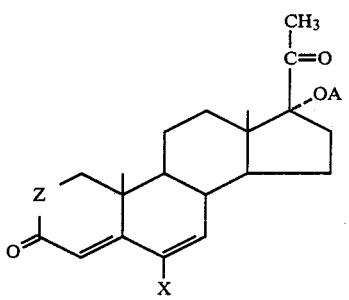

wherein A represents a hydrogen atom or a lower alkanoyl group, Z represents an oxygen atom or the group

in which R represents a hydrogen atom or a lower alkyl group, and X represents a halogen atom, a process for production thereof, and the use thereof as a medicament, particularly as an antiandrogenic agent.

It has already been known that 17α-acetoxy-2-oxapregna-4,6-diene-3,20-dione having a methyl group at the 6-position has progestational activity (U.S. Pat. No. 3,080,381). It is also known that 2-oxapregnane-3,20-dione having a cyano group at the 5-position has antiandrogenic activity (British Pat. No. 1,277,754).

With a regard to a 2-azapregnane-type compound, J. Org. Chem., 31 (7), 2109 (1966) discloses 2-aza-5α-pregnane-3,20-dione, but fails to describe its pharmacological activity.

It has now been found in accordance with this invention that the 2-oxa-or -aza-pregnane compounds of formula (I) above are novel compounds not described in the prior literature, and because of their very strong antiandrogenic activity, are useful as a drug for the prevention, therapy and treatment of androgen-dependent diseases such as prostatic hypertrophy, prostatic cancer, alopecea, acne and seborrhea.

In addition, the compounds of formula (I) show a progesterone-like action, and can be used as a drug for preventing abortion or for contraception.

The term "lower", as used in the present specification and claims, means that a group or a compound qualified by this term has not more than 6 carbon atoms.

The "lower alkanoyl group" represented by A in formula (I) includes, for example, acetyl, propionyl, butyryl, isobutyryl, valeryl and hexanoyl groups. The acetyl group is preferred. Where Z represents

R is preferably a hydrogen atom, but may be a lower alkyl group. Examples of the "lower alkyl group" represented by R are methyl, ethyl, n-propyl, isopropyl, n-butyl, isobutyl, sec-butyl, and tert-butyl groups. The methyl group is preferred. The "halogen atom" represented by X includes fluorine, chlorine and bromine atoms. The chlorine atom is preferred.

Typical examples of the compounds of formula (I) provided by this invention include
17α-acetoxy-6-chloro-2-oxapregna-4,6-diene-3,20-dione,
6-chloro-17α-hydroxy-2-oxapregna-4,6-diene-3,20-dione,
6-chloro-2-oxa-17α-propionyloxypregna-4,6-diene-3,20-dione,
17α-butyryloxy-6-chloro-2-oxapregna-4,6-diene-3,20-dione,
6-chloro-2-oxa-17α-valeryloxypregna-4,6-diene-3,20-dione,
6-chloro-17α-hexanoyloxy-2-oxapregna-4,6-diene-3,20-dione,
17α-acetoxy-6-fluoro-2-oxapregna-4,6-diene-3,20-dione,
6-fluoro-2-oxa-17α-propionyloxypregna-4,6-diene-3,20-dione,
6-fluoro-17α-hexanoyloxy-2-oxapregna-4,6-diene-3,20-dioene,
17α-acetoxy-6-bromo-2-oxapregna-4,6-diene-3,20-dione,
17α-acetoxy-2-aza-6-chloropregna-4,6-diene-3,20-dione,
2-aza-6-chloro-17α-hyroxypregna-4,6-diene-3,20-dione,
2-aza-6-chloro-17α-propionyloxypregna-4,6-diene-3,20-dione,
2-aza-17α-butyryloxy-6-chloropregna-4,6-diene-3,20-dione,
2-aza-6-chloro-17α-valeryloxypregna-4,6-diene-3,20-dione,
2-aza-6-chloro-17α-hexanoyloxypregna-4,6-diene-3,20-dione,
17α-acetoxy-2-aza-6-chloro-2-methylpregna-4,6-diene-3,20dione,
17α-acetoxy-2-aza-6-chloro-2-ethylpregna-4,6-diene-3,20-dione,
17α-acetoxy-2-aza-6-fluoropregna-4,6-diene-3,20-dione,
2-aza-6-fluoro-17α-hexanoyloxypregna-4,6-diene-3,20-dione, and
17α-acetoxy-2-aza-6-bromopregna-4,6-diene-3,20-dione.

Of these compounds, 17α-acetoxy-6-chloro-2-oxapregna-4,6-diene-3,20-dione and 17α-acetoxy-2-aza-6-chloropregna-4,6-diene-3,20-dione are especailly suitable from the standpoint of pharmacological properties.

The compounds of formula (I) can be produced in accordance with the following reaction scheme.

Reaction Scheme
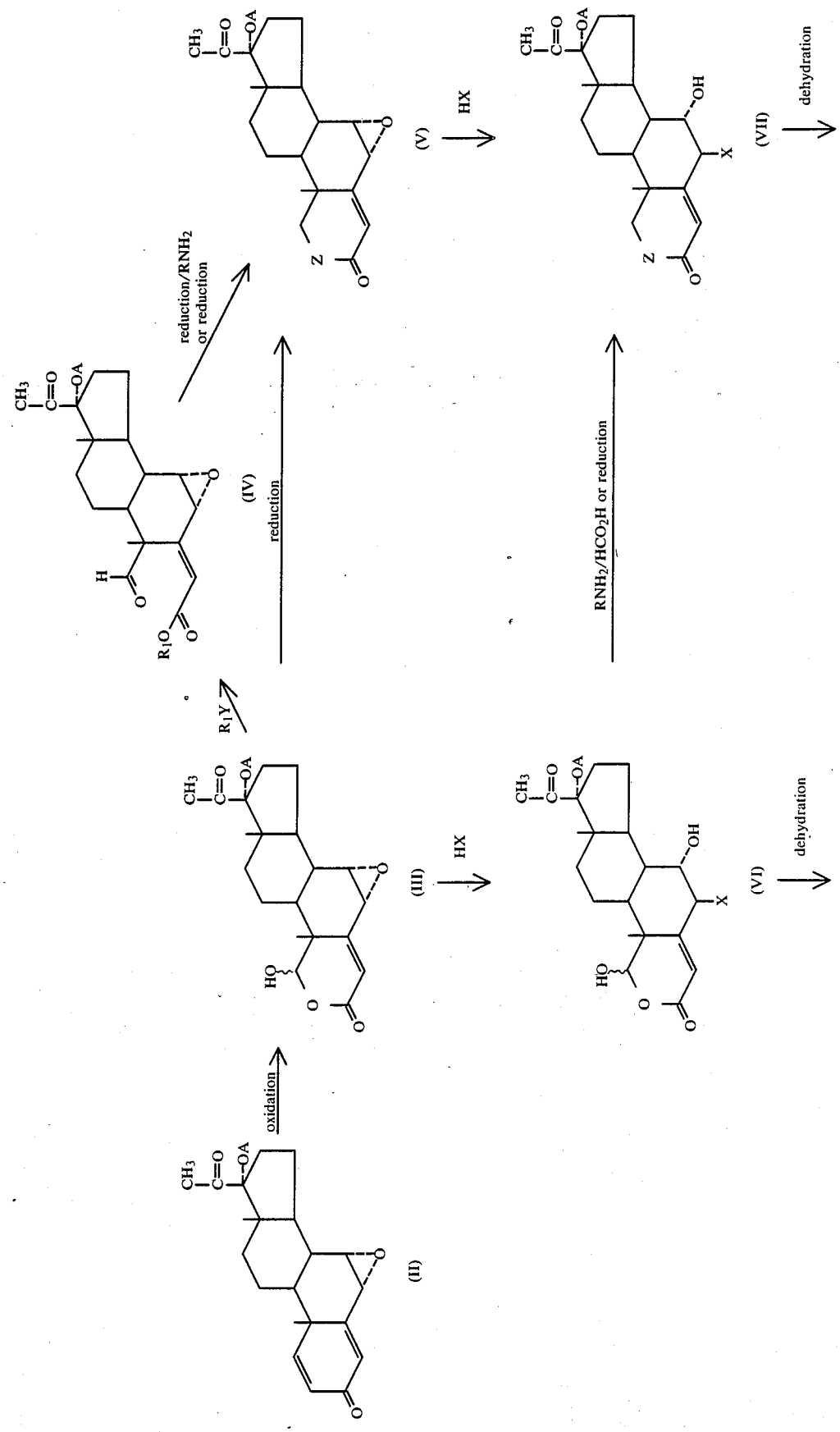

-continued
Reaction Scheme
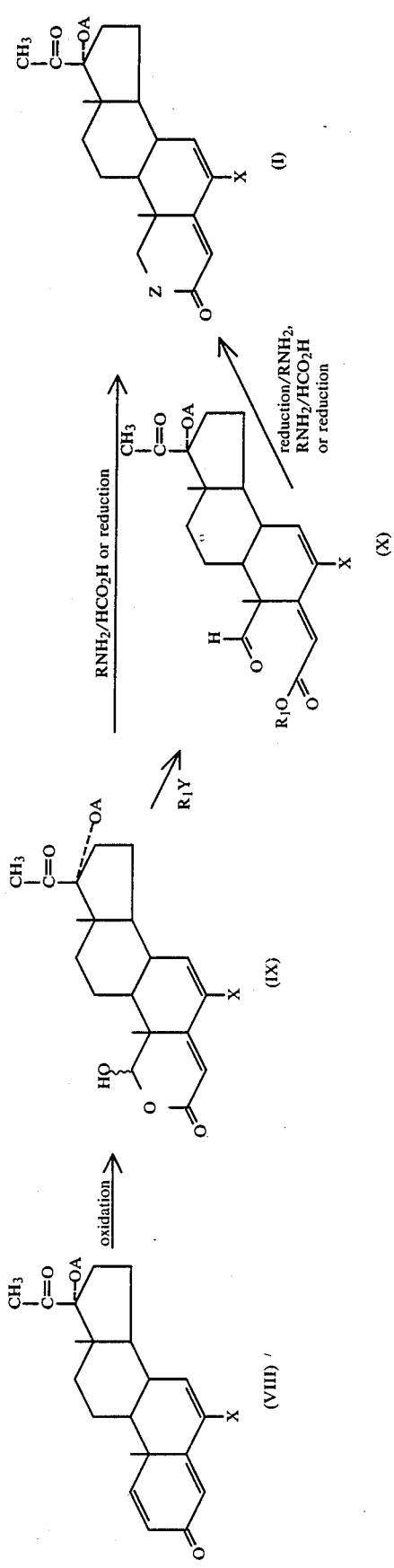

In the above formulae, A, Z, X and R are as defined above; $R_1$ represents a lower alkyl group; and Y represents an iodine or bromine atom.

In the above scheme, the oxidation of the compound of formula (II) can usually be carried out at a temperature of from about −80° C. to the refluxing temperature of the reaction mixture using an oxidizing agent such as ozone, osmium tetroxide or a mixture of osmium tetroxide with an oxidation aid such as potassium chlorate, lead tetraacetate or potassium periodate in a solvent, for example an ether such as dioxane or tetrahydrofuran, a halogenated hydrocarbon such as dichloromethane or chloroform, an alcohol such as t-butanol or amyl alcohol, pyridine, or a mixture of water with such an organic solvent.

The resulting compound of formula (III) can be converted to the compound of formula (IV) by, for example, reacting it with a reagent of the formula $R_1Y$ such as methyl iodide or ethyl iodide in the presence of a silver salt. This reaction can be carried out in the absence of a solvent using an excess of the above reagent, or in a solvent, for example a halogenated hydrocarbon such as chloroform or carbon tetrachloride, or an ether such as tetrahydrofuran or dioxane, generally at the refluxing temperature of the reaction mixture.

The resulting compound of formula (IV) can be coverted to the compound of formula (V) by reducing it in the presence (when Z is

or absence (when Z=O) of ammonia or a primary amine of the formula $R-NH_2$. The reduction can generally be carried out at a temperature of from about −20° C. to room temperature using a complex metal hydride such as sodium borohydride, potassium borohydride, sodium cyanoborohydride or lithium t-butoxyaluminohydride, optionaly in the presence of an inorganic salt or an organic acid salt in a solvent, for example, an alcohol such as methanol or ethanol, an ether such as tetrahydrofuran or dioxane or a mixture of water with such an organic solvent. The amount of ammonia or the primary amine represented by the formula $R-NH_2$ is generally about 1 to 20 moles, per mole of the compound of formula (IV).

The compound of formula (V) in which Z=O may alternatively be produced directly by reducing the compound of formula (III). This reduction can also be carried out at a temperature of from about −20° C. to room temperature using such a complex metal hydride as illustrated above, optionally in the presence of an inorganic salt or an organic acid salt, in such a solvent as illustrated above.

The compound of formula (V) obtained can be converted to the compound of formula (VII) by reacting it with a hydrogen halide (HX) at about −20° C. to the refluxing temperature of the reaction mixture, usually at room temperature, in the absence of solvent or in a suitable inert solvent, for example an organic acid such as acetic acid or propionic acid, an alcohol such as ethanol or t-butanol, an ether such as tetrahydrofuran or dioxane, or a halogenated hydrocarbon such as chloroform or carbon tetrachloride.

Subsequent dehydration of the compound of formula (VII) so obtained can give the compound of formula (I) in accordance with this invention. This dehydration may usually be carried out by treating the compound of formula (VII) with a dehydrating agent such as p-toluenesulfonic acid, phosphorus oxychloride, p-toluenesulfonyl chloride, methanesulfonyl chloride or thionyl chloride in a solvent, for example an organic base such as pyridine, an aromatic hydrocarbon such as benzene or toluene, a halogenated hydrocarbon such as chloroform or carbon tetrachloride at a temperature of from room temperature to the refluxing temperature of the reaction mixture.

As an alternative route, the compound of formula (I) can be produced from the compound of formula (VIII) as a starting material. In this alternative route, the oxidation of the compound of formula (VIII) can be carried out in the same way as described above with regard to the oxidation of the compound of formula (II). The reaction of the resulting compound of formula (IX) with the reagent of the formula $R_1Y$ can also be carried out in the same way as described above with regard to the reaction of the compound of formula (III) with the reagent of formula $R_1Y$. The compound of formula (X) so obtained is reduced in the absence or presence of ammonia or the primary amine of the formula $R-NH_2$ in the same way as described above with regard to the reduction of the compound of formula (IV), whereupon the desired compound of formula (I) can be obtained.

The compound of formula (X) can also be converted to the desired compound of formula (I) by reacting it with ammonia or the primary amine of the formula $R-NH_2$ in the presence of formic acid. This reaction can be carried out generally at the refluxing temperature of the reaction mixture in the absence of a solvent, usually using a large excess of formic acid.

The amount of ammonia or the primary amine of the formula $R-NH_2$ is generally about 1 to 20 moles per mole of the compound of formula (X).

The compound of formula (IX) can be converted directly to the compound of formula (I) by reducing it or by reacting it with ammonia or the primary amine of the formula $R-NH_2$ in the presence of formic acid. This reaction can also be carried out in the same way as described above with regard to the reduction of the compound of formula (IV) or the reaction of the compound of formula (X) with the compound of formula $R-NH_2$ in the presence of formic acid.

The intermediate of formula (VII) can also be produced by treating the compound of formula (III) with a hydrogen halide and thereafter reducing the treated compound or reacting it with ammonia or the primary amine of the formula $R-NH_2$ in the presence of formic acid. The reaction of the compound of formula (III) with the hydrogen halide, the reduction of the resulting compound of formula (VI), and the reaction of the compound of formula (VI) with the compound of the formula $R-NH_2$ in the presence of formic acid may be carried out in the same way as described above with respect to the reaction of the compound of formula (V) with the hydrogen halide, the reduction fo the compound of formula (IV), and the reaction of the compound of formula (X) with the compound of the formula $R-NH_2$ in the presence of formic acid.

The intermediate of formula (IX) can also be synthesized by dehydrating the compound of formula (VI). Dehydration of the compound of formula (VI) can be carried out in the same way as described above with regard to the dehydration of the compound of formula (VII).

A compound of formula (I) in which A is a hydrogen atom can be converted to the corresponding compound of formula (I) in which A is a lower alkanoyl group by lower alkanoylation in a manner known per se. The compound of formula (I) in which A is a lower alkanoyl group can be converted to the correspondiang compound of formula (I) in which A is a hydrogen atom by hydrolysis in a manner known per se.

Lower alkanoylation of the compound of formula (I) in which A is a hydrogen atom can be carried out, for example, buy it with a reactive derivative of a lower alkanoic acid, such as an acid, anhydride or acid halide thereof, at a temperature from room temperature to the refluxing temperature of the reaction mixture in the absence of solvent or in an inert solvent, for example an ether such as diethyl ether, tetrahydrofuran or dioxane, a halogenated hydrocarbon such as chloroform or carbon tetrachloride, or an aromatic hydrocarbon such as benzene or toluene, optionally in the presence of an acid catalyst such as p-toluenesulfonic acid or perchloric acid.

The compound of formula (I) produced as above can be isolated and purified by means known per se, for example filtration, recrystallization, column chromatography or thin-layer chromatography (TLC).

The 2-oxa-, -aza-pregnane compounds of formula (I) provided by this invention have excellent antiandrogenic activity, and are useful, for example, as a therapeutic agent for prostatic hypertrophy; a therapeutic agent for prostatic cancer; a therapeutic agent for premature, presenile, senile or areatus seborrheic or pityroid alopecia; a hair-nourishing agent; or a therapeutic agent for acne vulgaris.

The compounds of formula (I) also have a pregesterone-like action, and can be used as a drug for prevention of abortion or for contraception.

The compounds of formula (I) provided by this invention are characterized by having no adrenal gland inhibiting activity.

The following experiments demonstrate the excellent antiandrogenic activity and progestational activity of the compounds of formula (I) provided by this invention.

The compounds of this invention used in the following examples are designated by the following symbols.

A: 17α-acetoxy-6-chloro-2-oxapregna-4,6-diene-3,20-dione

B: 6-chloro-2-oxa-17α-propionyloxypregna-4,6-diene-3,20-dione

C: 17α-acetoxy-2-aza-6-chloropregna-4,6-diene-3,20-dione,

D: 17α-acetoxy-2-aza-6-chloro-2-methylpregna-4,6-diene-3,20-dione.

(1) Measurement of antiandrogenic activity (by subcutaneous and oral administrations)

Male young rats of the Wistar strain were castrated, and divided into groups each consisting of 5 rats. One group was not-treated. Testosterone propionate (androgen) was subcutaneously administered daily in a dise of 0.05 mg/day to another group over one week. To still another group, the test compound was administered subcutaneously or orally, and at the same time, testosterone propionate was subcutaneously administered daily in a dose of 0.05 mg/day over one week. Thereafter, the animals were anatomized, and the prostate was removed, and weighed. The ratio of the effect of the test compound to that of chlormnadinone acetate (to be abbreviated as CMA hereinafter) as an active control was determined. The results are tabulated below.

| Test compound | Antiandrogenic activity (CMA = 1) | |
|---|---|---|
| A | 5.0 | (sc) |
|   | 10.6 | (po) |
| B | 3.9 | (sc) |
|   | 7.8 | (po) |
| C | 3.9 | (sc) |
| D | 1 | (sc) |

(2) Measurement of progestational activity

Young female rabbits (body weight 680 to 1279 g), five per group, were used and the test was conducted by the Clauberg-Mcphail method [K. Kontula et al., Acta Endocrinol. 78, 574 (1975)].

Estradiol benzoate was subcutaneously administered to the animals in a dose of 2 micrograms/head once a day over 7 days, and for the next 5 days, the test compound was subcutaneously administered twice daily (once on the first day), and once on the morning of the 6th day (10 times in total). The estradiol benzoate was used as a solution in sesame oil, and the test compound was used as a suspension in physiological saline containing 2% of Tween 80. In the afternoon of the 6th day, the animals were sacrificed. The uterus was weighed, and the width of endometrium and the width of myometrium were also evaluated microscopically. The results showed that compound A of this invention showed more than 100 times as much progestational activity as progesterone.

(3) Toxicity

A suspension of the test compound in physiological saline containing 2% Tween 80 was orally administered to Wistar-strain male rats (6 weeks old) divided into groups each consisting of 5 rats, and the animals were observed for 72 hours. As a result, no case of death was observed even when the compound A of the invention was administered in a dose of 3000 mg/kg.

The compounds of formula (I) provided by this invention can thus be administered as medicaments orally, parenterally (e.g., intramuscularly, intravenously, subcutaneously, or intrarectally) or topically for the therapy and treatment of humans and other mammals.

When used as medicaments, the compounds of this invention may be formulated into various forms suitable for oral, parenteral or topical administration. For example, the compounds of this invention can be formulated by using ordinary pharmaceutically acceptable nontoxic adjuvants such as a vehicle, binder, lubricant, disintegrant, antiseptic, isotonic, stabilizer, dispersant, antioxidant, coloring agent, flavor or buffer.

Such a medicament can be formulated into a solid form (such as tablets, hard capsules, soft capsules, granules, powders, pellets, pills or trouches), a semisolid form (such as suppositories and ointments) and a liquid form (injectable preparations, emulsions, suspensions, lotions or sprays) depending upon its use. Examples of the nontoxic pharmaceutically acceptable adjuvants include starch, gelatin, glucose, lactose, fructose, maltose, magnesium carbonate, talc, magnesium stearate, methyl cellulose, carboxymethyl cellulose or its salt, gum arabic, polyethylene glycol, alkyl p-hydroxybenzoates, syrup, ethanol, propylene glycol, vaseline, carbowax, glycerol, sodium chloride, sodium sulfite, sodium phosphate and citric acid. These medicaments can also contain therapeutically useful other drugs.

The content of the compound of this invention in the medicament may be varied depending upon the form of the medicament. Generally, it is desirably 1 to 100% by weight for the solid and semisolid forms, and 0.1 to 10% by weight for the liquid form.

The dosage of the compound of this invention may be varied widely depending upon the kind of a subject which is a human or another mammal, the route of administration, the severity of the condition of the subject, the diagnosis of a physician, etc. Generally, it is about 0.01 to 10 mg/kg/day. It is of course possible to administer the compound of the invention in dosages outside the above range depending upon the severity of the condition of the patient or the physician's diagnosis. The dosage for one day may be applied once, or portionwise several times.

The following Examples and Formulation Examples illustrate the present invention more specifically.

EXAMPLE 1

Sodium borohydride (72 mg) was added to a mixture of 200 mg of 17α-acetoxy-6-chloro-1ξ-hydroxy-2-oxapregna-4,6-diene-3,20-dione, 80 mg of sodium hydrogen carbonate, 20 ml of methanol and 10 ml of water, and the mixture was stirred at room temperature for 30 minutes. Concentrated hydrochloric acid (about 0.4 ml) was added to the reaction mixture, and the mixture was extracted with ethyl acetate. The extract was washed with a saturated aqueous solution of sodium hydrogen carbonate, and dried over anhydrous magnesium sulfate. The solvent was evaporated under reduced pressure. The crude product was purified by TLC [developing solvent: chloroform)] to give 120 mg of 17α-acetoxy-6-chloro-2-oxapregna-4,6-diene-3,20-dione.

Melting point: 253°–255° C.

IR (KBr, cm$^{-1}$): 3390, 1710, 1605, 1245.

$^1$H-NMR (CDCl$_3$, δ): 0.72 (3H, s) 1.21 (3H, s), 2.05 (3H, s), 2.09 (3H, s), 4.11 and 4.21 (2H, ABq, J=11 Hz), 6.15 (1H, s), 6.30 (1H, broad s).

MS (m/z): 406 (M+), 363, 346, 321, 303.

EXAMPLE 2

A mixture of 70 mg of 17α-acetoxy-6β-chloro-7α-hydroxy-2-oxa-4-0regnene-3,20-dione, 400 mg of p-toluenesulfonyl chloride, 1 ml of 4-dimethylaminopyridine and 0.9 ml of pyridine was heated under reflux for 2 hours. Water was added to the reaction mixture, and the mixture was extracted with ethyl acetate. The extract was washed with 50% hydrochloric acid and then with a saturated aqueous solution of sodium hydrogen carbonate, and dried over anhydrous magnesium sulfate. The solvent was evaporated, and the crude product was purified by TLC [developing solvent: chloroform/acetone (19/1)] to give 52 mg of 17α-acetoxy-6-chloro-2-oxapregna-4,6-diene-3,20-dione. The $^1$H-NMR spectrum of this compound was the same as that of the compound produced in Example 1.

EXAMPLE 3

A mixture of 1.76 g of 17α-acetoxy-6β-chloro-7α-hydroxy-2-oxa-4-pregnene-3,20-dione, 1.11 ml of methanesulfonyl chloride and 5.2 ml of pyridine was stirred for 1 hour under ice cooling, and then for 12 hours at room temperature. Ice-cooled water was added to the reaction mixture, and the precipitated crystals were collected by filtration to give 2.01 g of 17α-acetoxy-6β-chloro-7α-mesyloxy-2-oxa-4-pregnene-3,20-dione.

Melting point: 225.5°–226.4° C.

IR (KBr, cm$^{-1}$): 1735, 1350, 1250, 1175.

$^1$H-NMR (CDCl$_3$, δ): 0.74 (3H, s), 1.48 (3H, s), 2.06 (3H, s), 2.09 (3H, s), 3.08 (3H, s), 4.11 and 4.28 (2H, ABq, J=10 Hz), 4.78 (1H, d, J=3 Hz), b 4.92 (1H, m), 6.02 (1H, s).

A mixture of 2.35 g of 17α-acetoxy-6β-chloro-7α-mesyloxy-2-oxa-4-pregnene-3,20-dione, 0.83 g of potassium acetate and 0.88 ml of dimethyl sulfoxide was stirred at room temperature for 12 hours. Ice-cooled water was poured into the reaction mixture, and the precipitated crystals were collected by filtration to give 1.37 g of 17α-acetoxy-6-chloro-2-oxapregna-4,6-diene-3,20-dione. The $^1$H NMR spectrum of this compound was the same as that of the compound produced in Example 1.

EXAMPLE 4

Methyl 17α-acetoxy-6-chloro-1,20-dioxo-A-nor-1,2-secorpregna-3,6-dien-2-oate (36 mg) was dissolved in 1 ml of tetrahydrofuran, and the solution was cooled with ice. To the solution was added 63 mg of lithium tri-t-butoxyaluminohydride with stirring under ice cooling, and the mixture was stirred for 15 minutes. A 20% aqueous solution of hydrogen chloride was added to the reaction mixture, and the mixture was extracted with chloroform. The extract was washed with a saturated aqueous solution of sodium hydrogen carbonate, and dried over anhydrous magnesium sulfate. The solvent was evaporated, and the crude product was purified by TLC [developed solvent: chloroform/acetone (100/1)] to give 23 mg of 17α-acetoxy-6-chloro-2-oxapregna-4,6-diene-3,20-dione. The $^1$H-NMR spectrum of this compound was the same as that of the compound produced in Example 1.

EXAMPLE 5

A mixture of 116 mg of 17α-acetoxy-6-chloro-2-oxapregna-4,6-diene-3,20-dione, 0.5 ml of an about 28% methanol solution of sodium methylate, 0.1 ml of tetrahydrofuran and 5 ml of methanol was heated at 70° C. for 10 minutes. Water was added to the reaction mixture, and the mixture was extracted with ethyl acetate. The extract was washed with a 30% aqueous solution of hydrogen chloride and then with a saturated aqueous solution of sodium hydrogen carbonate, and dried over anhydrous magnesium sulfate. The solvent was evaporated, and the crude product was purified by TLC [developing solvent: chloroform/acetone (19/1)] to give 70 mg of 6-chloro-17α-hydroxy-2-oxapregna-4,6-diene-3,20-dione.

Melting point: 218°–221° C.

IR (KBr, cm$^{-1}$): 3410, 1700, 1605.

$^1$H-NMR (CDCl$_3$, δ): 0.75 (3H, s), 1.20 (3H, s), 2.24 (3H, s), 4.08 and 4.19 (2H, ABq, J=13 Hz), 6.11 (1H, s), 6.34 (1H, broad s).

MS (m/z): 364 (M+), 321, 303.

EXAMPLE 6

A mixture of 70 mg of 6-chloro-17α-hydroxy-2-oxapregna-4,6-diene-3,20-dione and 2 ml of propionic anhydride was heated at 130° C. for 6 hours. Water and pyridine were added to the reaction mixture, and the mixture was stirred at room temperature for 1 hour and then extracted with ethyl acetate. The extract was washed with a 30% aqueous solution of hydrogen chloride and then with a saturated aqueous solution of sodium hydrogen carbonate, and dried over anhydrous magnesium sulfate. The solvent was evaporated, and the crude product was purified by TLC [developing solvent: chloroform/acetone (19/1)] to give 54 mg of 6-chloro-2-oxa-17α-propionyloxypregna-4,6-diene-3,20-dione.

Melting point: 199°–202° C.
IR (KBr, cm$^{-1}$): 3380, 1700, 1600.
$^1$H-NMR (CDCl$_3$, δ): 0.73 (3H, s), 1.17 (3H, t, J=7 Hz), 1.22 (3H, s), 2.05 (3H, s), 2.38 (2H, q, J=7 Hz), 4.11 and 4.22 (2H, ABq, J=12 Hz), 6.17 (1H, s), 6.32 (1H, broad s).
MS (m/z): 420 (M$^+$), 377, 346, 321, 303.

EXAMPLE 7

Example 6 was repeated except that caproic anhydride was used instead of propionic anhydride. There was obtained 6-chloro-17α-hexanoyloxy-2-oxapregna-4,6-diene-3,20-dione.

$^1$H-NMR (CDCl$_3$, δ): 0.73 (3H, s), 0.91 (3H, t, J=6 Hz), 1.22 (3H, s), 2.05 (3H, s), 4.11 and 4.21 (2H, ABq, J=11 Hz), 6.17 (1H, s), 6.32 (1H, broad s).
MS (m/z): 462 (M$^+$), 321, 303.

EXAMPLE 8

A mixture of 100 mg of 17α-acetoxy-6α,7α-epoxy-2-oxa-4-pregnene-3,20-dione, 200 mg of potassium hydrogen fluoride and 1 ml of dimethyl sulfoxide was heated at 140° C. for 20 minutes. Water was added to the reaction mixture, and the mixture was extracted with ethyl acetate. The extract was washed with a saturated aqueous solution of sodium hydrogen carbonate, and dried over anhydrous magnesium sulfate. The solvent was evaporated, and the crude product was purified by TLC [developing solvent: chloroform/acetone (50/1)] to give 20 mg of 17α-acetoxy-6-fluoro-2-oxapregna-4,6-diene-3,20-dione.

$^1$H-NMR (CDCl$_3$, δ): 0.72 (3H, s), 1.22 (3H, s), 2.05 (3H, s), 2.09 (3H, s), 4.17 (2H, m), 5.70 (1H, broad d, J=14 Hz), 5.96 (1H, s).
MS (m/z): 390 (M$^+$), 347, 330, 305, 287.

EXAMPLE 9

A mixture of 500 mg of methyl 17α-acetoxy-6-chloro-1,20-dioxo-A-nor-1,2-secopregna-3,6-dien-2-oate, 1.3 g of ammonium acetate, 1.0 g of sodium cyanoborohydride, 5 mol of tetrahydrofuran and 9 ml of methanol was stirred at room temperature for 22 hours. About 20 ml of a 50% aqueous solution of hydrogen chloride was added to the reaction mixture, and the mixture was stirred at room temperature for 1 hour, and extracted with chloroform. The extract was washed with a saturated aqueous solution of sodium hydrogen carbonate, and dried over anhydrous magnesium sulfate. The solvents were evaporated, and the crude product was purified by TLC [developing solvent: chloroform/methanol (19/1)] to give 295 mg of 17α-acetoxy-2-aza-6-chloropregna-4,6-diene-3,20-dione as a colorless crystalline powder.

Melting point: 286.6°–287.6° C.
IR (KBr, cm$^{-1}$): 3400, 1725, 1660.
$^1$H-NMR (CDCl$_3$, δ): 0.71 (3H, s), 1.17 (3H, s), 2.06 (3H, s), 2.10 (3H, s), 3.27 (2H, m), 6.14 (1H, broad s), 6.23 (1H, broad s), 6.77 (1H, broad s).
MS (m/z): 405 (M$^+$), 320, 302.

EXAMPLE 10

Example 9 was repeated except that methylamine hydrochloride and a 30% ethanol solution of methylamine were used instead of ammonium acetate. There was obtained 17α-acetoxy-2-aza-6-chloro-2-methylpregna-4,6-diene-3,20-dione.

Melting point: 292.6°–293.6° C.
IR (KBr, cm$^{-1}$): 3400, 1725, 1650.
$^1$H-NMR (CDCl$_3$, δ): 0.71 (3H, s), 1.12 (3H, s), 2.06 (3H, s), 2.09 (3H, s), 3.02 (3H, s), 3.12 and 3.33 (2H, ABq, J=13 Hz), 6.13 (1H, s), 6.14 (1H, s).
MS (m/z): 419 (M$^+$), 359, 334, 316.

EXAMPLE 11

A mixture of 300 mg of 17α-acetoxy-6-chloro-1ξ-hydroxy-2-oxapregna-4,6-diene-3,20-dione, 3.5 g of ammonium formate and 4 ml of 99% formic acid was heated under reflux for 28 hours. Water was added to the reaction mixture, and the mixture was extracted with ethyl acetate. The extract was washed successively with an aqueous solution of sodium hydroxide, a 30% aqueous solution of hydrogen chloride and a saturated aqueous solution of sodium hydrogen carbonate, and then dried over anhydrous magnesium sulfate. The solvent was evaporated, and the crude product was purified by TLC [developing solvent: chloroform/acetone (6/1)] to obtain 50 mg of 17α-acetoxy-2-aza-6-chloropregna-4,6-diene-3,20-dione having an Rf value of about 0.5. The $^1$H-NMR spectrum of this compound was the same as that of the compound produced in Example 9. Furthermore, 30 mg of 2-aza-6-chloro-17α-hydroxypregna-4,6-diene-3,20-dione having an Rf value of about 0.3 was obtained.

$^1$H-NMR (CDCl$_3$, δ): 0.75 (3H, s), 1.13 (3H, s), 2.25 (3H, s), 3.24 (2H, m), 6.09 (1H, broad s), 6.21 (1H, broad s), 6.77 (1H, broad s).
MS (m/z): 363 (M$^+$), 320.

EXAMPLE 12

A mixture of 80 mg of 17α-acetoxy-2-aza-6-chloro-2-methylpregna-4,6-diene-3,20-dione, 0.5 ml of a 30% methanol solution of sodium methylate, 3 ml of tetrahydrofuran and 1 ml of methanol was heated at 60° C. for 30 minutes. Water was added to the reaction mixture, and the mixture was extracted with chloroform. The extract was washed with water, and dried over anhydrous magnesium sulfate. The crude product was purified by TLC [developing solvent: chloroform/acetone (9/1)] to give 55 mg of 2-aza-6-chloro-17α-hydroxy-2-methylpregna-4,6-diene-3,20-dione.

$^1$H-NMR (CDCl$_3$, δ): 0.77 (3H, s), 1.12 (3H, s), 2.27 (3H, s), 3.01 (3H, s), 1.17 and 3.33 (2H, ABq, J=12 Hz), 6.12 (1H, s), 6.15 (1H, broad s).
MS (m/z): 377 (M$^+$), 359, 334.

EXAMPLE 13

A mixture of 15 mg of 2-aza-6-chloro-17α-hydroxy-2-methylpregna-4,6-diene-3,20-dione and 0.5 ml of propionic anhydride was heated at 130° C. for 6 hours. The reaction mixture was cooled to room temperature, and about 0.5 ml of pyridine and about 0.5 ml of water were added. The mixture was left to stand at room temperature for 15 hours, and then extracted with ethyl acetate. The extract was washed with a 50% aqueous solution of hydrogen chloride and then with a saturated aqueous solution of sodium hydrogen carbonate, and dried over anhydrous magnesium sulfate. The solvent was evaporated, and the crude product was purified by TLC [developing solvent: chloroform/acetone (9/1)] to give 14 mg of 2-aza-6-chloro-2-methyl-17α-propionyloxypregna-4,6-diene-3,2-dione.

¹H-NMR (CDCl₃, δ): 0.71 (3H, s), 1.12 (3H, s), 1.17 (3H, t, J=7 Hz), 2.05 (3H, s), 3.38 (2H, q, J=7 Hz), 3.03 (3H, s), 3.12 and 3.33 (2H, ABq, J=13 Hz), 6.13 (1H, s), 6.14 (1H, s).

EXAMPLE 14

A mixture of 15.0 g of 17α-acetoxy-6-chloropregna-1,4,6-triene-3,20-dione, 0.5 g of osmium tetroxide, 33.6 g of sodium periodate, 300 ml of dioxane and 98 ml of water was heated under reflux for 3 hours. Periodic acid (16 g) was added to the reaction mixture, and the mixture was further refluxed for 30 minutes. The reaction mixture was added to 4 liters of 5% sodium thiosulfate and extracted with ethyl acetate. The extract was washed with water, and dried over anhydrous magnesium sulfate. The solvent was evaporated, and the crude product was purified by silica gel column chromatography (eluent: chloroform) to give 7.2 g of 17α-acetoxy-6-chloro-1ξ-hydroxy-2-oxapregna-4,6-diene-3,20-dione.

Melting point: 276°–278° C.

IR (KBr, cm⁻¹): 3510, 1725, 1616, 1258.

¹H-NMR (CDCl₃, δ): 0.72 (3H, s), 1.20 (3H, s), 2.06 (3H, s), 2.12 (3H, s), 5.51 (1H, s), 6.21 (1H, s), 6.35 (1H, broad s).

MS (m/z): 422 (M+), 380, 376, 362, 337, 319.

EXAMPLE 15

A mixture of 4.6 g of 17α-acetoxy-6-chloro-1ξ-hydroxy-2-oxapregna-4,6-diene-3,20-dione, 23 g of silver oxide and 50 ml of methyl iodide was heated under reflux for 3 hours. The insoluble materials were removed by filtration, and the filtrate was distilled to give 4.19 g of methyl 17α-acetoxy-6-chloro-1,20-dioxo-A-nor-1,2-secopregna-3,6-dien-2-oate as a colorless crystalline powder.

¹H-NMR (CDCl₃, δ): 0.71 (3H, s), 1.48 (3H, s), 2.02 (3H, s), 2.08 (3H, s), 3.68 (3H, s), 6.32 (1H, broad s), 6.48 (1H, s), 9.57 (1H, s).

EXAMPLE 16

Two hundred milligrams of 17α-acetoxy-6α,7α-epoxypregna-1,4-diene-3,20-dione was dissolved in 15 ml of dichloromethane and 15 ml of pyridine, and ozone was passed into the solution at −78° C. for 10 minutes. The reaction mixture was stirred at room temperature for 10 minutes, and 3 ml of 10% sodium hydrogen sulfite was added to the mixture. The mixture was stirred at room temperature for 1 hour and extracted with chloroform. The extract was washed with 10% sulfuric acid and subsequently with a saturated aqueous solution of sodium hydrogen carbonate, and dried over anhydrous magnesium sulfate. The solvent was evaporated, and the crude product was purified by TLC [developing solvent: chloroform/acetone (9/1)] to give 146 mg of 17α-acetoxy-6α,7α-epoxy-1ξ-hydroxy-2-oxa-4-pregnene-b3,20-dione ¹H-NMR (CDCl₃-D₂O, δ): 0.70 (3H, s), 1.18 (3H, s), 2.05 (3H, s), 2.12 (3H, s), 3.47 (1H, d, J=4 Hz), 3.54 (1H, d, J=4 Hz), 5.43 (1H, s). 6.17 (1H, s).

EXAMPLE 17

A mixture of 185 mg of 17α-acetoxy-6α,7α-epoxy-1ξ-hydroxy-2-oxa-4-pregnene-3,2-dione, 68 mg of sodium hydrogen carbonate, 71 mg of sodium borohydride, 4.4 ml of tetrahydrofuran, 10 ml of methanol and 8.9 ml of water was stirred at room temperature for 30 minutes. To the reaction mixture was added 10% sulfuric acid, and the mixture was extracted with ethyl acetate. The extract was washed with a saturated aqueous solution of sodium hydrogen carbonate, and dried over anhydrous magnesium sulfate. The solvents were evaporated under reduced pressure to give 140 mg of 17α-acetoxy-6α,7α-epoxy-2-oxa-4-pregnene-3,20-dione.

¹H-NMR (CDCl₃, δ): 0.70 (3H, s), 1.18 (3H, s), 2.05 (3H, s), 2.11 (3H, s), 3.48 (1H, d, J=4 Hz), 3.52 (1H, d, J=4 Hz), 4.11 (2H, m), 6.10 (1H, s).

EXAMPLE 18

Concentrated hydrochloric acid (0.1 ml) was added to a solution of 97 mg of 17α-acetoxy-6α,7α-epoxy-2-oxa-4-pregnene-3,20-dione in 4 ml of tetrahydrofuran, and the solution was stirred at room temperature for 10 minutes. Water was added to the reaction mixture, and the mixture was extracted with ethyl acetate. The extract was washed with a saturated aqueous solution of sodium hydrogen carbonate, and dried over anhydrous magnesium sulfate. The solvent was evaporated under reduced pressure to give 102 mg of 17α-acetoxy-6β-chloro-7α-hydroxy-2-oxa-4-pregnene-3,20-dione.

¹H-NMR (CDCl₃, δ): 0.72 (3H, s), 1.46 (3H, s), 2.06 (3H, s), 2.11 (3H, s), 3.97 (1H, m), 4.11 and 4.28 (2H, ABq, J=11 Hz), 4.46 (1H, d, J=3 Hz), 5.97 (1H, s).

EXAMPLE 19

A mixture of 20 mg of 17α-acetoxy-6α,7α-epoxy-1ξ-hydroxy-2-oxa-4pregnene-3,20-dione and 3 ml of 16% hydrochloric acid-ethyl acetate solution was stirred at room temperature for 10 minutes. A saturated aqueous solution of sodium hydrogen carbonate was added to the reaction mixture, and the mixture was extracted with ethyl acetate. The extract was dried over anhydrous magnesium sulfate, and the solvent was evaporated to give 21 mg of 17α-acetoxy-6β-chloro-1ξ,7α-dihydroxy-2-oxa-4-pregnene-3,20dione.

¹H-NMR (CDCl₃, δ): 0.72 (3H, s), 1.43 (3H, s), 2.05 (3H, s), 2.12 (3H, s), 3.93 (1H, m), 4.54 (1H, d, J=4 Hz), 5.43 (1H, broad s), 6.05 (1H, s).

EXAMPLE 20

Sodium borohydride (64 mg) was added to a mixture of 170 mg of 17α-acetoxy-6β-chloro-1ξ,7α-dihydroxy-2-oxa-4-pregnene-3,20-dione, 62 mg of sodium hydrogen carbonate, 4 ml of tetrahydrofuran, 9.2 ml of methanol and 8.2 ml of water. The reaction mixture was stirred at room temperature for 30 minutes, and 4 ml of 50% hyrochloric acid was added. The mixture was extracted with ethyl acetate, and the extract was washed with a saturated aqueous solution of sodium hydrogen carbonate and dried over anhydrous magnesium sulfate. The solvent was evaporated, and the crude product was purified by TLC [developing solvent: chloroform/acetone (9/1)] to give 154 mg of 17α-acetoxy-6β-chloro-7α-hydroxy-2-oxa-4-pregnene-3,20-dione. The ¹H NMR spectrum of this compound was the same as that of the compound produced in Example 18.

The following Formulation Examples illustrate the preparation of medicaments containing the compound of this invention.

FORMULATION EXAMPLE A

| FORMULATION EXAMPLE A |
|---|
| Formulation of tablets |
| Recipe: 5 mg tablet |

-continued

| FORMULATION EXAMPLE A | |
|---|---|
| Formulation of tablets | |
| 17α-acetoxy-6-chloro-2-oxapregna-4,6-diene-3,20-dione | 5.0 |
| Starch | 11.7 |
| Lactose | 79.3 |
| Carboxymethyl cellulose calcium | 2.5 |
| Talc | 1.0 |
| Magnesium stearate | 0.5 |
| | 100.0 mg |

Crystals of 17α-acetoxy-6-chloro-2-oxapregna-4,6-diene-3,20-dione were pulverized to a particle size of less than 70 microns, and starch, lactose and carboxymethyl cellulose calcium were added and mixed well. A 10% starch paste was added to the mixed powder and they were mixed with stirring to produce granules. After drying, the particle size of the granules was adjusted to about 1000 microns, and talc and magnesium stearate were added. They were mixed and tableted.

FORMULATION EXAMPLE B

| FORMULATION EXAMPLE B | |
|---|---|
| Formulation of capsules | |
| Recipe: 10 mg capsule | |
| 17α-acetoxy-6-chloro-2-oxapregna-4,6-diene-3,20-dione | 10.0 |
| Starch | 50.0 |
| Lactose | 47.0 |
| Magnesium stearate | 3.0 |
| | 110.0 mg |

Crystals of 17α-acetoxy-6-chloro-2-oxapregna-4,6-diene-3,20-dione were well pulverized, and mixed with starch, lactose and magnesium stearate. After thorough mixing, the mixture was filled into No. 5 capsules.

What we claim is:

1. A method for inhibiting androgen in mammals in need of such inhibition which comprises administering to the mammals an effective amount of the compound of the formula

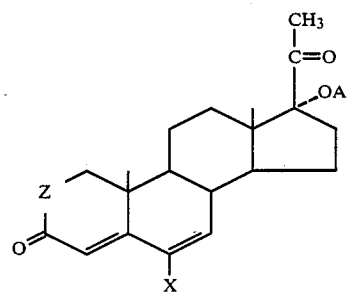

wherein A is a hydrogen atom or a lower alkanoyl group of 2 to 6 carbon atoms, Z is an oxygen atom or the group

in which R is a hydrogen atom or an alkyl group of up to 6-carbon atoms, and X is a halogen atom.

2. A method for supplying progestin in mammals in need of such supplying which comprises administering to the mammals an effective amount of the compound of the formula

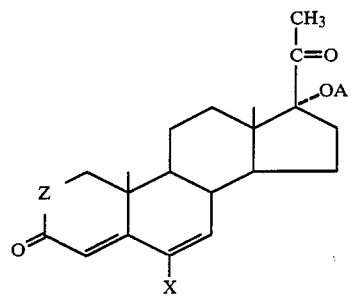

wherein A is a hydrogen atom or a lower alkanoyl group of 2 to 6 carbon atoms, Z is an oxygen atom or the group

in which R is a hydrogen atom or an alkyl group of up to 6-carbon atoms, and X is a halogen atom.

3. A pharmaceutical composition for inhibiting androgen which comprises an effective amount of the compound of the formula

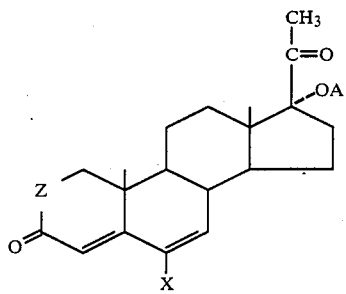

wherein A is a hydrogen atom or a lower alkanoyl group of 2 to 6 carbon atoms, Z is an oxygen atom or the group

in which R is a hydrogen atom or an alkyl group of up to 6-carbon atoms, and X is a halogen atom the active substance and a pharmaceutically acceptable carrier or diluent.

4. A pharmaceutical composition for supplying progestin which comprises an effective amount of the compound of the formula

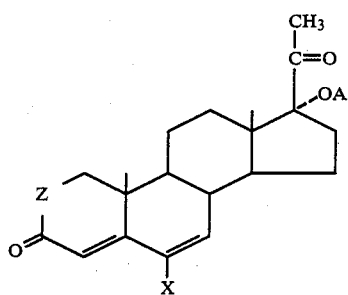

wherein A is a hydrogen atom or a lower alkanoyl group of 2 to 6 carbon atoms, Z is an oxygen atom or the group

in which R is a hydrogen atom or an alkyl group of up to 6-carbon atoms, and X is a halogen atom as the active substance and a pharmaceutically acceptable carrier or diluent.

5. Method according to claim 1 wherein Z is oxygen, A is $COCH_3$, and X is chlorine.

6. Method according to claim 2 wherein Z is oxygen, A is $COCH_3$, and X is chlorine.

7. The pharmaceutical composition according to claim 3 wherein Z is oxygen, A is $COCH_3$, and X is chlorine.

8. The pharmaceutical composition according to claim 4 wherein Z is oxygen, A is $COCH_3$, and X is chlorine.

* * * * *